US010946364B2

(12) United States Patent
Suh et al.

(10) Patent No.: US 10,946,364 B2
(45) Date of Patent: Mar. 16, 2021

(54) CATALYST SYSTEM FOR OXIDATIVE DEHYDROGENATION, REACTOR FOR OXIDATIVE DEHYDROGENATION INCLUDING CATALYST SYSTEM, AND METHOD OF PERFORMING OXIDATIVE DEHYDROGENATION USING REACTOR

(71) Applicant: LG CHEM, LTD., Seoul (KR)

(72) Inventors: Myungji Suh, Daejeon (KR); Dong Hyun Ko, Daejeon (KR); Jun Han Kang, Daejeon (KR); Hyunseok Nam, Daejeon (KR); Sang Jin Han, Daejeon (KR); Seongmin Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 16/327,151

(22) PCT Filed: Apr. 12, 2018

(86) PCT No.: PCT/KR2018/004273
§ 371 (c)(1),
(2) Date: Feb. 21, 2019

(87) PCT Pub. No.: WO2018/190642
PCT Pub. Date: Oct. 18, 2018

(65) Prior Publication Data
US 2019/0201876 A1    Jul. 4, 2019

(30) Foreign Application Priority Data

Apr. 12, 2017 (KR) .................. 10-2017-0047504
Apr. 11, 2018 (KR) .................. 10-2018-0042151

(51) Int. Cl.
*B01J 23/80* (2006.01)
*B01J 8/02* (2006.01)
(Continued)

(52) U.S. Cl.
CPC .............. *B01J 23/80* (2013.01); *B01J 8/02* (2013.01); *B01J 21/005* (2013.01); *B01J 21/04* (2013.01);
(Continued)

(58) Field of Classification Search
None
See application file for complete search history.

(56) References Cited

U.S. PATENT DOCUMENTS 3,284,536 A    11/1966    Bajars et al.
3,303,234 A     2/1967    Bajars et al.
(Continued)

FOREIGN PATENT DOCUMENTS

AU    2007274285    8/2010
CN    101328116    12/2008
(Continued)

OTHER PUBLICATIONS

KR 10-2012-0009687 English Translation (Year: 2012).*
(Continued)

*Primary Examiner* — Colin W. Slifka
(74) *Attorney, Agent, or Firm* — Dentons US LLP

(57) ABSTRACT

Provided is a catalyst system for oxidative dehydrogenation, a reactor for oxidative dehydrogenation including the catalyst system, and a method of performing oxidative dehydrogenation using the reactor. In the catalyst system, a fixed-bed reactor is filled with a catalyst for oxidative dehydrogenation in an n-stage structure (n being an integer of 2 or more), wherein each stage of the n-stage structure satisfies Equations 1 and 2 as claimed so that the concentration of an active ingredient included in the catalyst gradually increases in the direction in which reactants are fed into the reactor. Heat generated inside the reactor may be effectively controlled during oxidative dehydrogenation,
(Continued)

thereby improving conversion rate, selectivity, and yield. In addition, catalyst deterioration may be reduced, thereby improving long-term stability of the catalyst.

16 Claims, 2 Drawing Sheets

(51) Int. Cl.

| | | |
|---|---|---|
| *B01J 35/08* | (2006.01) | |
| *C07C 5/48* | (2006.01) | |
| *B01J 21/00* | (2006.01) | |
| *B01J 21/04* | (2006.01) | |
| *B01J 35/00* | (2006.01) | |
| *B01J 35/02* | (2006.01) | |
| *B01J 35/10* | (2006.01) | |
| *B01J 37/00* | (2006.01) | |
| *B01J 37/02* | (2006.01) | |
| *B01J 37/03* | (2006.01) | |
| *B01J 37/08* | (2006.01) | |
| *C07C 11/167* | (2006.01) | |

(52) U.S. Cl.
CPC ......... *B01J 35/0026* (2013.01); *B01J 35/023* (2013.01); *B01J 35/026* (2013.01); *B01J 35/08* (2013.01); *B01J 35/1076* (2013.01); *B01J 37/0036* (2013.01); *B01J 37/0225* (2013.01); *B01J 37/0236* (2013.01); *B01J 37/038* (2013.01); *B01J 37/08* (2013.01); *C07C 5/48* (2013.01); *C07C 11/167* (2013.01); *B01J 2208/025* (2013.01); *C07C 2521/04* (2013.01); *C07C 2523/745* (2013.01); *C07C 2523/80* (2013.01)

(56) References Cited

U.S. PATENT DOCUMENTS

| | | | |
|---|---|---|---|
| 3,998,760 | A | 12/1976 | Christmann et al. |
| 4,150,064 | A | 4/1979 | Miklas |
| 4,469,589 | A | 9/1984 | Yoo et al. |
| 6,563,000 | B1 | 5/2003 | Yunoki et al. |
| 2006/0004229 | A1 | 1/2006 | Dieterle et al. |
| 2010/0121123 | A1 | 5/2010 | Chung et al. |
| 2010/0298601 | A1 | 11/2010 | Choi et al. |
| 2011/0004041 | A1 | 1/2011 | Chung et al. |
| 2012/0130137 | A1 | 5/2012 | Orita et al. |
| 2013/0158325 | A1 | 6/2013 | Kwon et al. |
| 2014/0066680 | A1 | 3/2014 | Miao et al. |
| 2014/0163288 | A1 | 6/2014 | Ruttinger et al. |
| 2015/0073184 | A1 | 3/2015 | Caciula et al. |
| 2016/0023963 | A1 | 1/2016 | Maat et al. |
| 2018/0186711 | A1 | 7/2018 | Suh et al. |
| 2018/0214854 | A1 | 8/2018 | Choi et al. |
| 2018/0333702 | A1 | 11/2018 | Suh et al. |
| 2019/0016649 | A1 | 1/2019 | Kim et al. |
| 2019/0329226 | A1 | 10/2019 | Suh et al. |
| 2020/0079710 | A1 | 3/2020 | Jamaleddine et al. |

FOREIGN PATENT DOCUMENTS

| | | | | |
|---|---|---|---|---|
| CN | 101918126 | | 12/2010 | |
| EP | 3488921 A2 | | 5/2019 | |
| JP | S462063 | | 10/1971 | |
| JP | S51-125001 | | 11/1976 | |
| JP | 2008504309 | | 2/2008 | |
| JP | 2011-006395 | | 1/2011 | |
| JP | 2013536066 | | 9/2013 | |
| JP | 2014198707 | | 10/2014 | |
| JP | 2018-524159 | | 8/2018 | |
| KR | 10-0847206 | | 7/2008 | |
| KR | 10-2012-0009687 | * | 2/2012 | ............ B01J 23/889 |
| KR | 10-2012-0026049 | | 3/2012 | |
| KR | 10-2013-0046458 | | 5/2013 | |
| KR | 10-2014-0082869 | | 7/2014 | |
| KR | 10-1508776 | | 3/2015 | |
| KR | 10-2017-0068351 | | 6/2017 | |
| WO | 2012-011659 | | 1/2012 | |
| WO | 2014/138520 | | 9/2014 | |
| WO | 2017-046680 | | 3/2017 | |
| WO | 2017-150830 | | 9/2017 | |
| WO | 2019-013473 | | 1/2019 | |

OTHER PUBLICATIONS

International Search Report and the Written Opinion of PCT/KR2018/004273, dated Nov. 8, 2018.
U.S. Appl. No. 16/477,866.
Office Action of Chinese Patent Office in Appl'n. No. 201880003266.8, dated Dec. 11, 2020.
Office Action of Korean Patent Office in Appl'n No. 10-2017-0162431, dated Nov. 17, 2020.
Lee, "Preparation, characterization, and catalytic activity of ferrite catalysts for oxidative dehydrogenation of n-butene to 1,3-butadiene," Thesis (Masters), 1st Seoul National University Graduate School (2009) [English Language Abstract included].

* cited by examiner

CATALYST SYSTEM FOR OXIDATIVE DEHYDROGENATION, REACTOR FOR OXIDATIVE DEHYDROGENATION INCLUDING CATALYST SYSTEM, AND METHOD OF PERFORMING OXIDATIVE DEHYDROGENATION USING REACTOR

CROSS-REFERENCE TO RELATED APPLICATIONS

This application is the National Stage Application of International Application No. PCT/KR2018/004273, filed on Apr. 12, 2018, which claims priority to Korean Patent Application No. 10-2017-0047504, filed on Apr. 12, 2017, and Korean Patent Application No. 10-2018-0042151, re-filed on Apr. 11, 2018, based on the priority of the above patent, in the Korean Intellectual Property Office, the disclosures of each of which are incorporated herein by reference.

TECHNICAL FIELD

The present invention relates to a catalyst system for oxidative dehydrogenation, a reactor for oxidative dehydrogenation including the catalyst system, and a method of performing oxidative dehydrogenation using the reactor. More specifically, the present invention relates to a catalyst system for oxidative dehydrogenation, in which a reactor is filled with a catalyst for oxidative dehydrogenation so that the concentration of an active ingredient included in the catalyst gradually increases in the direction in which reactants are fed into the reactor. According to the catalyst system of the present invention, heat generated inside a reactor may be efficiently controlled, whereby conversion rate, selectivity, and yield may be greatly improved and the long-term stability of a catalyst may be improved.

BACKGROUND ART 1,3-butadiene, a major basic fraction, is a representative raw material used in preparation of synthetic rubber, and the price thereof fluctuates rapidly in connection with supply and demand of the petrochemical industry. Examples of the method of preparing 1,3-butadiene include naphtha cracking, direct dehydrogenation of normal butene, oxidative dehydrogenation of normal butene, and the like.

According to the method of preparing 1,3-butadiene by oxidative dehydrogenation of normal butene, butene and oxygen react in the presence of a metal oxide catalyst to generate 1,3-butadiene and water. In this case, water generated as a result of the reaction is stable. Thus, the method is thermodynamically very advantageous. In addition, since oxidative dehydrogenation of normal butene is an exothermic reaction unlike direct dehydrogenation, reaction can be performed at a low temperature. Thus, 1,3-butadiene may be obtained in high yield while reducing energy consumption. In addition, in the case of oxidative dehydrogenation, since an oxidizing agent is added, generation of carbon deposits which shorten the catalyst life by poisoning the catalyst is reduced. Further, since removal of the oxidizing agent is easy, the method of preparing 1,3-butadiene using oxidative dehydrogenation is very suitable for commercialization.

However, heat generated during oxidative dehydrogenation is accumulated in a catalyst bed, deteriorating a catalyst, thereby degrading catalyst life, and side reaction is promoted by excess heat, thereby reducing reaction efficiency. As a result, butadiene yield, selectivity for butadiene, and the conversion rate of butene may be lowered.

To solve these problems, a method of controlling space velocity by controlling the amount of gas fed to a reactor has been proposed. However, this method was unsatisfactory in terms of productivity and yield. Thus, development of a system for oxidative dehydrogenation of butene that can effectively control heat generated inside a reactor while having high productivity is still required.

PRIOR ART DOCUMENT

[Patent Document] KR 10-1508776 B1

DISCLOSURE

Technical Problem

Therefore, the present invention has been made in view of the above problems, and it is one object of the present invention to provide a catalyst system for oxidative dehydrogenation that may effectively control heat generated inside a reactor to prevent catalyst deterioration, thereby improving conversion rate, selectivity, and yield.

It is another object of the present invention to provide a reactor for oxidative dehydrogenation including the catalyst system for oxidative dehydrogenation and a method of performing oxidative dehydrogenation using the reactor.

The above and other objects can be accomplished by the present disclosure described below.

Technical Solution

In accordance with one aspect of the present invention, provided is a catalyst system for oxidative dehydrogenation including a fixed-bed reactor filled with a catalyst for oxidative dehydrogenation in an n-stage structure (n being an integer of 2 or more), wherein each stage of the n-stage structure satisfies Equations 1 and 2 below:

$$X \text{ wt \%} + Y \text{ wt \%} = 100 \text{ wt \%}, \qquad \text{[Equation 1]}$$

wherein X is an amount of $AB_2O_4$ and is 5 or more and less than 30, wherein A is one or more metals selected from the group consisting of copper (Cu), radium (Ra), barium (Ba), strontium (Sr), calcium (Ca), beryllium (Be), zinc (Zn), magnesium (Mg), manganese (Mn), and cobalt (Co), and B is iron (Fe); and Y is an amount of a porous support and is more than 70 and 95 or less; and $$X_n > X_{n-1}, \qquad \text{[Equation 2]}$$

wherein, with respect to the direction in which reactants are fed into the reactor, $X_n$ represents an amount of X present in the n-th stage, and $X_{n-1}$ represents an amount of X present in the (n−1)th stage.

In accordance with another aspect of the present invention, provided is a reactor for oxidative dehydrogenation including the catalyst system for oxidative dehydrogenation.

In accordance with yet another aspect of the present invention, provided is a method of performing oxidative dehydrogenation including a step of performing oxidative dehydrogenation in the reactor for preparing butadiene of the present invention while continuously passing reactants containing a C4 compound including normal butene through the catalyst bed of the reactor.

Advantageous Effects

As apparent from the foregoing, the present invention advantageously provides a catalyst system for oxidative dehydrogenation, in which a reactor is filled with a catalyst for oxidative dehydrogenation so that the concentration of an active ingredient included in the catalyst gradually increases in the direction in which reactants are fed into the reactor. When the catalyst system according to the present invention is used, it is possible to effectively control distribution of heat generated inside a reactor during oxidative dehydrogenation without adding a separate apparatus or changing the conventional manufacturing facilities, and thus to improve conversion rate, selectivity, and yield. In addition, catalyst deterioration can be reduced, thereby improving the long-term stability of a catalyst.

BEST MODE

Figure 1:
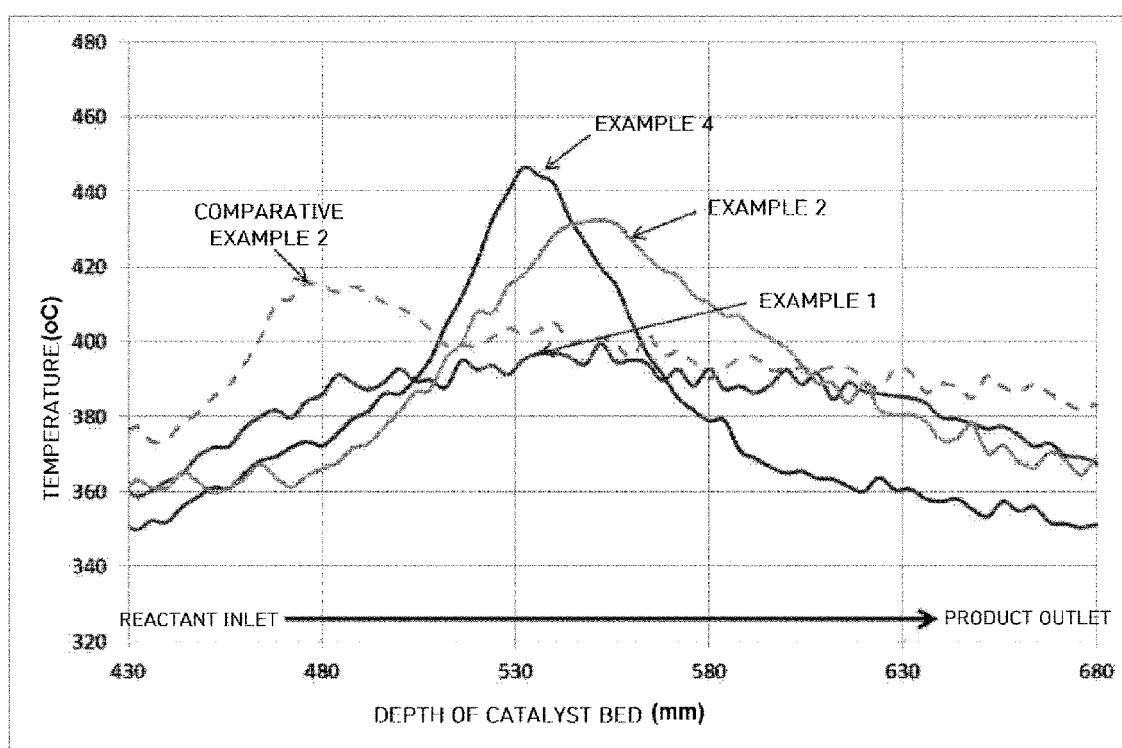
FIG. 1 is a graph showing the temperature distribution inside a catalyst bed when oxidative dehydrogenation is performed using the catalyst systems according to Examples and Comparative Examples of the present invention.

Hereinafter, the catalyst for oxidative dehydrogenation according to the present invention system will be described in detail.

The catalyst system for oxidative dehydrogenation according to the present invention includes a fixed-bed reactor filled with a catalyst for oxidative dehydrogenation in an n-stage structure (n being an integer of 2 or more), wherein each stage of the n-stage structure satisfies Equations 1 and 2 below:

$$X \text{ wt \%} + Y \text{ wt \%} = 100 \text{ wt \%},$$  [Equation 1]

wherein X represents a content is an amount of $AB_2O_4$ and is 5 or more and less than 30, wherein A is one or more metals selected from the group consisting of copper (Cu), radium (Ra), barium (Ba), strontium (Sr), calcium (Ca), beryllium (Be), zinc (Zn), magnesium (Mg), manganese (Mn), and cobalt (Co), and B is iron (Fe); and Y is an amount of a porous support and is more than 70 and 95 or less; and $$X_n > X_{n-1},$$  [Equation 2]

wherein, with respect to the direction in which reactants are fed into the reactor, $X_n$ is an amount of X present in for the n-th stage, and $X_{n+1}$ is an amount of X present in the (n−1)th stage.

In the present invention, $AB_2O_4$ is the active ingredient of the catalyst for oxidative dehydrogenation. That is, the catalyst for oxidative dehydrogenation is a coating catalyst having a porous support coated with $AB_2O_4$ as an active ingredient.

For example, $AB_2O_4$ can be a zinc ferrite ($ZnFe_2O_4$), wherein A is zinc (Zn), and B is iron (Fe). $AB_2O_4$ exhibits excellent activity in oxidative dehydrogenation of normal butene. When $AB_2O_4$ is used, selectivity for 1,3-butadiene may be excellent.

For example, $AB_2O_4$ can have an average particle diameter of 250 μm or less, 1,000 μm or less, 45 μm or less, 0.1 to 250 μm, 0.1 to 75 μm, 100 to 250 μm, or 45 to 250 μm. Within this range, the catalyst has excellent activity, and thus reaction efficiency may be improved.

For example, the catalyst for oxidative dehydrogenation filled in each stage of the fixed-bed reactor preferably includes $AB_2O_4$ in an amount of 5 wt % or more and less than 30 wt %, 7 to 27 wt %, 7 to 20 wt %, 7 to 18 wt %, or 7 to 14 wt %. Within this range, reaction efficiency may be excellent, and yield, selectivity, and conversion rate may be improved.

For example, the porous support can have an average particle diameter of 3 to 9 mm, 3 to 7 mm, or 4 to 6 mm. Within this range, reaction efficiency is excellent, and thus conversion rate and selectivity may be improved.

For example, the porous support may have an average pore size of 50 to 200 μm or 100 to 150 μm. Within this range, the catalyst may be easily coated with $AB_2O_4$ powder, and desorption of the powder may be prevented.

In the present invention, average particle diameter and average pore size may be measured using, for example, a scanning electron microscope.

For example, the porous support can have a packing density of 0.4 to 3 g/cm$^3$ or more than 0.4 and less than 3 g/cm$^3$, preferably 0.7 to 2.0 g/cm$^3$, more preferably 0.8 to 1.5 kg/m$^3$ or 0.9 to 1.3 kg/m$^3$. In this case, coating ratio is determined based on packing density.

In the present invention, packing density is calculated by dividing mass capable of filling 100 cc into a graduated cylinder by the volume value of 100 cc.

In the present invention, average particle diameter may be measured using, for example, a scanning electron microscope.

The shape of the porous support is preferably spherical, hollow, or in the form of pellets. In this case, reaction efficiency is excellent, and thus yield, selectivity, and conversion rate may be improved.

For example, the porous support can be one or more selected from the group consisting of alumina, silica, and zirconia, preferably alumina or silica. In this case, the mechanical strength required to fill a reactor may be appropriate, and side reaction may be reduced.

When necessary, the coating catalyst of the present invention can optionally include an organic or inorganic binder. In this case, the binder can be contained in an amount of 30 parts by weight or less, 0.1 to 20 parts by weight, or 0.1 to 10 parts by weight based on 100 parts by weight of $AB_2O_4$. Within this range, the wear resistance of the catalyst may be improved without significantly lowering the reaction efficiency of oxidative dehydrogenation.

For example, the binder can include aluminum-silicate, methylcellulose, hydroxypropyl methylcellulose, or both. When the binder is contained in an appropriate amount, the wear resistance of the catalyst may be improved without significantly lowering the reaction efficiency of oxidative dehydrogenation.

As another example, the coating catalyst of the present invention can be a binder-free catalyst. In this case, side reaction, which may be caused by a binder, does not occur, and thus the conversion rate of normal butene and selectivity for butadiene may be greatly improved. In addition, feed of a certain component may be omitted, thereby shortening the production process of the catalyst and reducing production costs.

In the present invention, binder-free indicates that, when a catalyst is prepared, an organic or inorganic binder is not included and/or a catalyst is prepared without a binder.

For example, the fixed-bed reactor is filled with the catalyst for oxidative dehydrogenation according to the present invention in a 2- to 8-stage (n is 2 to 8), 3- to 8-stage, 3- to 6-stage, or 3- to 5-stage structure. Within this range, distribution of heat generated inside the reactor is effectively controlled without significantly increasing process costs.

Thus, when butadiene is prepared, conversion rate, selectivity, and yield may be greatly improved, and the long-term stability of the catalyst may be improved.

For example, the catalyst system of the present invention satisfies Equation 3 below. In this case, excessive heat generation is effectively prevented during reaction. As a result, when butadiene is prepared, conversion rate, selectivity, and yield may be improved, and the long-term stability of the catalyst may be improved.

$$(X_n - X_{n-1}) \geq 2 \quad \text{[Equation 3]}$$

(in Equation 3, $X_n$ is an amount of X present in the n-th stage, and $X_{n-1}$ is an amount of X present in the (n−1)th stage).

For example, Equation 3 can be expressed as $(X_n - X_{n-1}) > 2$, $20 \geq (X_n - X_{n-1}) \geq 2$, or $20 \geq (X_n - X_{n-1}) > 2$. In this case, excessive heat generation is prevented during reaction. Therefore, when butadiene is prepared, conversion rate, selectivity, and yield may be improved, and at the same time, the long-term stability of the catalyst may be improved.

For example, the catalyst system of the present invention satisfies Equation 4 below. In this case, deterioration of the catalyst due to excess heat may be prevented. Thus, when butadiene is prepared, conversion rate, selectivity, and yield may be improved, thereby increasing productivity.

$$(Y_{n-1} - Y_n) \geq 2 \quad \text{[Equation 4]}$$

(in Equation 4, $Y_n$ is an amount of Y present in the n-th stage, and $Y_{n-1}$ is an amount of Y present in the (n−1)th stage).

For example, Equation 4 can be expressed as $(Y_{n-1} - Y_n) > 2$, $20 \geq (Y_{n-1} - Y_n)$ 2, or $20 \geq (Y_{n-1} - Y_n) > 2$. In this case, excessive heat generation is prevented during reaction. Thus, when butadiene is prepared, conversion rate, selectivity, and yield may be improved, and at the same time, the long-term stability of the catalyst may be improved.

The catalyst system can be a catalyst system for oxidative-dehydrogenation for preparing 1,3-butadiene.

In addition, the present invention provides a reactor for preparing butadiene including the catalyst system and a method of preparing 1,3-butadiene using the reactor.

For example, the method of preparing 1,3-butadiene according to the present invention includes i) a step of filling a reactor with a catalyst for oxidative dehydrogenation in a stationary phase; and ii) a step of performing oxidative dehydrogenation while continuously passing reactants containing a C4 compound including normal butene through the catalyst bed of a reactor filled with the catalyst, wherein the reactor in step i) is a fixed-bed reactor filled with a catalyst for oxidative dehydrogenation in an n-stage structure (n being an integer of 2 or more), wherein each stage of the n-stage structure satisfies Equations 1 and 2.

For example, the C4 mixture includes one or more selected from normal butene isomers including 2-butene (trans-2-butene and cis-2-butene) and 1-butene, and can optionally further include normal butane or C4 raffinate-3.

For example, the reactants can further include one or more selected from air, nitrogen, steam, and carbon dioxide, preferably nitrogen and steam.

As a specific example, the reactants can include a C4 mixture, oxygen, steam, and nitrogen in a molar ratio of 1:0.1 to 1.5:1 to 15:0.5 to 10, 1:0.5 to 1.2:5 to 12:0.5 to 5, 1:1.0 to 1.2:5 to 12:0.5 to 5, or 1:1.2 to 1.5:5 to 12:0.5 to 5. In addition, the method of preparing butadiene according to the present invention is advantageous in that reaction efficiency is excellent and the amount of waste water generated is reduced even though steam is used in small quantities, i.e., steam is used in an amount of 1 to 10 or 5 to 10 mol based on 1 mol of the C4 mixture. Thus, waste water treatment costs and energy consumed in the process may be reduced.

For example, the oxidative dehydrogenation reaction can be performed at reaction temperature of 250 to 500° C., 300 to 450° C., 320 to 400° C., or 330 to 380° C. Within this range, reaction efficiency may be improved without significantly increasing energy consumption, and thus the productivity of 1,3-butadiene may be increased.

For example, the oxidative dehydrogenation reaction can be performed at a gas hourly space velocity (GHSV) of 50 to 2,000 $h^{-1}$, 50 to 1,500 $h^{-1}$, or 50 to 1,000 $h^{-1}$ based on normal butene. Within this range, reaction efficiency is excellent, and thus conversion rate, selectivity, and yield may be excellent.

In the present invention, a reactor including the catalyst system for oxidative dehydrogenation can be used as the reactor of the present invention without particular limitation. For example, the reactor can be a multi-tubular reactor, a plate reactor, or the like.

For example, the amount of the catalyst loaded into the reactor can be 10 to 90% by volume based on the total volume of the interior of the reactor.

Hereinafter, the present invention will be described in more detail with reference to the following preferred examples. However, these examples are provided for illustrative purposes only and should not be construed as limiting the scope and spirit of the present invention. In addition, it will be apparent to those skilled in the art that various changes and modifications may be made without departing from the spirit and scope of the present invention, and such changes and modifications are also within the scope of the appended claims.

Preparation Example

1. Preparation of $ZnFe_2O_4$ Powder

An aqueous metal precursor solution containing 2 L of distilled water, 288.456 g of zinc chloride ($ZnCl_2$), and 1,132.219 g of iron chloride ($FeCl_3$) was prepared. The metal precursor solution was added dropwise to a coprecipitation bath containing 2 L of distilled water, and at the same time, 9 wt % aqueous ammonia was added thereto to adjust the pH to 8. To obtain a sample having a uniform composition, all of the metal precursor solution was added dropwise with stirring for 1 hour using an agitator, aged for 1 hour, and then the solution was filtered to separate precipitate. The separated precipitate was dried for 16 hours, and then burned at 650° C. to obtain $ZnFe_2O_4$ powder, and the obtained powder was pulverized.

2. Preparation of Coating Catalyst $ZnFe_2O_4$ powder prepared according to the ratio shown in Tables 1 to 3 was dispersed in distilled water to obtain a catalyst slurry having a concentration of about 10 to 30 wt %. Alumina balls having an average particle diameter of 5 mm were coated with the prepared catalyst slurry. After the coating process was completed, a coating catalyst was prepared by drying the catalyst slurry-coated alumina balls in an oven at 90 to 120° C. so that distilled water was evaporated.

EXAMPLES

Example 1

The coating catalyst according to Preparation Example is loaded into a reactor in an incremental manner in a five-stage structure as shown in Table 1 below. Then, the conversion rate of butene, 1,3-selectivity for butadiene, the yield of 1,3-butadiene, and selectivity for COx were measured.

The C4 mixture containing trans-2-butene and cis-2-butene, oxygen, steam, and nitrogen as reactants were mixed in a molar ratio of 1:1:5:4. At this time, the amount of each of the C4 mixture, oxygen, and nitrogen was controlled using a mass flow controller, and the injection rate of steam was controlled using a liquid pump. In addition, the prepared coating catalyst was loaded into a tubular reactor in a stationary phase. The feed rate of reactants was set so that a gas hourly space velocity (GHSV) was 120 h$^{-1}$ based on normal butene in the C4 mixture. The reaction was performed at the reaction temperature shown in Table 1 below.

TABLE 1

| GHSV/mole ratio of butene:oxygen:steam:nitrogen = 120/1:1:5:4, 355° C. | |
|---|---|
| X [content of ZnFe$_2$O$_4$, wt %] | Y [content of porous support, wt %] |
| First stage | 3 | 97 |
| Second stage | 6 | 94 |
| Third stage | 9 | 91 |
| Fourth stage | 14 | 86 |
| Fifth stage | 27 | 73 |

In Table 1, each of X and Y is based on 100% by weight of the total amount thereof.

Example 2

The catalyst composition was loaded into a reactor in an incremental manner in a three-stage structure as shown in Table 2 below. Then, reaction was performed under the same conditions and in the same manner as in Example 1, except that the reaction was performed at the temperature specified in Table 2 below.

TABLE 2

| GHSV/mole ratio of butene:oxygen:steam:nitrogen = 120/1:1:5:4, 360° C. | |
|---|---|
| X [content of ZnFe$_2$O$_4$, wt %] | Y [content of porous support, wt %] |
| First stage | 6 | 94 |
| Second stage | 9 | 91 |
| Third stage | 14 | 86 |

In Table 2, each of X and Y is based on 100% by weight of the total amount thereof.

Example 3

Reaction was performed under the same conditions and in the same manner as in Example 2, except that the molar ratio of butene:oxygen:steam:nitrogen was 1:1.2:5:4.

Example 4

The catalyst composition was loaded into a reactor in an incremental manner in a three-stage structure as shown in Table 3 below. Then, reaction was performed under the same conditions and in the same manner as in Example 1, except that a reaction temperature was 347° C.

TABLE 3

| GHSV/mole ratio of butene:oxygen:steam:nitrogen = 120/1:1:5:4, 347° C. | |
|---|---|
| X [content of ZnFe$_2$O$_4$, wt %] | Y [content of porous support, wt %] |
| First stage | 9 | 91 |
| Second stage | 14 | 86 |
| Third stage | 27 | 73 |

In Table 3, each of X and Y is based on 100% by weight of the total amount thereof.

Example 5

Reaction was performed under the same conditions and in the same manner as in Example 4, except that the molar ratio of butene:oxygen:steam:nitrogen was 1:1.2:5:4.

Comparative Example 1

ZnFe$_2$O$_4$ powder was prepared and pulverized in the same manner as in Examples, and the pulverized powder was kneaded with distilled water and an alcohol and then extrusion-molded to obtain pellets having a diameter of 2 mm and a length of 2 mm, followed by drying at 90° C. for 4 hours to obtain a catalyst in the form of pellets. 6% by volume of the prepared catalyst was mixed with 94% by volume of alumina balls, and the mixture was loaded into a reactor. Then, reaction was performed under the same conditions and in the same manner as in Example 1, except that a reaction temperature was set to 365° C.

Comparative Example 2

Reaction was performed under the same conditions and in the same manner as in Comparative Example 1, except that a reaction temperature was set to 375° C.

Test Example

The products according to Examples and Comparative Examples were analyzed using gas chromatography. The conversion rate of butene, the yield of 1,3-butadiene, and selectivity for 1,3-butadiene or COx were calculated according to Equations 7, 8, and 9 below, respectively. The results are shown in Table 4.

In addition, when oxidative dehydrogenation was performed using the catalyst systems according to Examples and Comparative Examples of the present invention, in a thermo-well at the center of a reactor, the temperature distribution inside a catalyst bed was analyzed while moving a thermocouple from the inlet of the reactor to the outlet of the reactor at a constant velocity of 4 mm per second (see FIG. 1 below).

Conversion rate (%)=[(Number of moles of butene reacted)/(Number of moles of butene supplied)]×100    [Equation 7]

Selectivity (%)=[(Number of moles of 1,3-butadiene or COx generated)/(Number of moles of butene reacted)]×100    [Equation 8]

Yield (%)=[(Number of moles of 1,3-butadiene generated)/(Number of moles of butene supplied)]×100    [Equation 9]

TABLE 4

|  | Conversion rate of butene (%) | Selectivity for 1,3-butadiene (%) | Yield of 1,3-butadiene (%) | Selectivity for COx (%) |
|---|---|---|---|---|
| Example 1 | 86.6 | 88.3 | 76.5 | 10.7 |
| Example 2 | 86.8 | 88.7 | 77.0 | 10.3 |
| Example 3 | 88.0 | 88.0 | 77.4 | 11.1 |
| Example 4 | 86.7 | 88.4 | 76.6 | 10.6 |
| Example 5 | 88.6 | 87.8 | 77.8 | 11.2 |
| Comparative Example 1 | 79.6 | 89.3 | 71.1 | 9.1 |
| Comparative Example 2 | 83.9 | 88.4 | 74.2 | 10.2 |

In the case of Examples 1 to 5, oxidative dehydrogenation was performed using a catalyst system including a reactor filled with a catalyst in a three- or five-stage structure, wherein the proportion of the catalyst coated on the porous support of the reactor was gradually increased with increase in layer number. As shown in Table 4, when the catalyst system according to the present invention was used, the conversion rate of butene, selectivity for 1,3-butadiene, and the yield of 1,3-butadiene were significantly superior to those of Comparative Examples 1 and 2, even though oxidative dehydrogenation was performed at a relatively low reaction temperature as compared with Comparative Examples 1 and 2.

In particular, in the case of Examples 3 and 5, in which a catalyst was loaded into a reactor in a three stage-structure, and the ratio of oxygen was slightly higher than in the other examples, the conversion rate of butene and selectivity for 1,3-butadiene were excellent. These results indicate that, when the amount of oxygen fed is increased to a certain extent, the phenomenon that reaction efficiency and the long-term stability of the catalyst are lowered due to increased selectivity for side reaction and increase in heat generation may be prevented.

In addition, referring to FIG. 1, when the catalyst system according to the present invention is used, the temperature distribution of a catalyst bed due to reaction heat generated during oxidative dehydrogenation exhibits a symmetrical distribution about the center of the catalyst bed. This result shows that the catalyst system is stable.

In conclusion, when the catalyst system according to the present invention is used, the productivity of butadiene may be improved and manufacturing costs may be reduced without adding any other device or changing equipment. In addition, since the catalyst system exhibits a stable temperature gradient during oxidative dehydrogenation, the phenomenon of deterioration of a catalyst due to excessive heat generation may be reduced, and as a result, the lifespan of a catalyst may be increased.

Additional Example 1

The catalyst composition of Example 1 was loaded into a reactor in an incremental manner in a three-stage structure as shown in Table 5 below. Then, reaction was performed under the same conditions and in the same manner as in Example 1, except that a reaction temperature was set to 347° C.

TABLE 5

| | GHSV/mole ratio of butene:oxygen:steam:nitrogen = 120/1:1:5:4, 347° C. | |
|---|---|---|
| Classification | X [content of ZnFe$_2$O$_4$, wt %] | Y [content of porous support, wt %] |
| First stage | 12 | 88 |
| Second stage | 14 | 86 |
| Third stage | 16 | 84 |

In Table 5, each of X and Y is based on 100% by weight of the total amount thereof.

Reference Example

The catalyst composition according to Example 1 was loaded into a reactor in an incremental manner in a three-stage structure as shown in Table 6 below. Then, reaction was performed under the same conditions and in the same manner as in Example 1, except that a reaction temperature was set to 347° C.

TABLE 6

| | GHSV/mole ratio of butene:oxygen:steam:nitrogen = 120/1:1:5:4, 347° C. | |
|---|---|---|
| Classification | X [content of ZnFe$_2$O$_4$, wt %] | Y [content of porous support, wt %] |
| First stage | 13 | 87 |
| Second stage | 14 | 86 |
| Third stage | 15 | 85 |

In Table 6, each of X and Y is based on 100% by weight of the total amount thereof.

Test Example

The products according to Additional Example 1 and Reference Example were analyzed using gas chromatography. The conversion rate of butene, the yield of 1,3-butadiene, and selectivity for 1,3-butadiene or COx were calculated according to Equations 7, 8, and 9, respectively. The results are shown in Table 7 below.

In addition, when oxidative dehydrogenation is performed using the catalyst systems according to Additional Example 1 and Reference Example, in a thermo-well at the center of a reactor, the temperature distribution inside a catalyst bed was analyzed while moving a thermocouple from the inlet of the reactor to the outlet of the reactor at a constant velocity of 4 mm per second (see FIG. 2 below).

TABLE 7

| Classification | Conversion rate of butene (%) | Selectivity for 1,3-butadiene (%) | Yield of 1,3-butadiene (%) | Selectivity for COx (%) |
|---|---|---|---|---|
| Additional Example 1 | 86.9 | 88.5 | 76.9 | 10.4 |
| Reference Example | 83.8 | 87.6 | 73.4 | 11.5 |

In the case of Additional Example 1 and Reference Example, oxidative dehydrogenation was performed using a catalyst system including a reactor filled with a catalyst in a three-layer structure, wherein the proportion of the catalyst coated on the porous support of the reactor was increased by 2% by weight or 1% by weight, respectively, with increase in layer number. In this case, as shown in Table 7, the conversion rate of butene, selectivity for 1,3-butadiene, and the yield of 1,3-butadiene were excellent, even though oxidative dehydrogenation was performed at a relatively low reaction temperature. However, in the case of Additional Example 1, in which the proportion of the catalyst was increased by 2% by weight with increase in layer number, the conversion rate of butene, selectivity for 1,3-butadiene, and the yield of 1,3-butadiene were excellent as compared with Reference Example, in which the proportion of the catalyst was increased by 1% by weight with increase in layer number.

Figure 2:
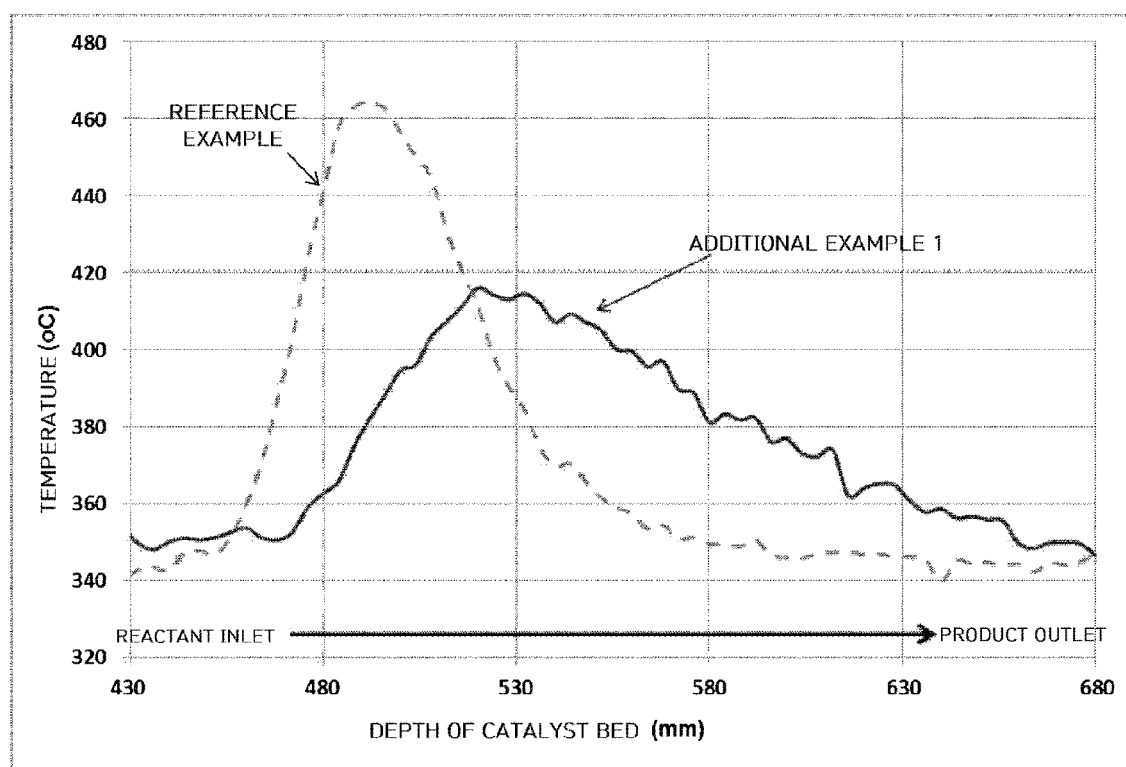
FIG. 2 is a graph showing the temperature distribution inside a catalyst bed when oxidative dehydrogenation is performed using the catalyst systems according to Additional Example 1 and Reference Example of the present invention.

In addition, as shown in FIG. 2, when the catalyst system of Reference Example is used, the temperature distribution of a catalyst bed due to reaction heat generated during oxidative dehydrogenation is biased toward the inlet of the reactor, whereas in the case of Additional Example 1, the temperature distribution of a catalyst bed is symmetrical about the center of the catalyst bed. Thus, in the case of Additional Example 1, the reaction process may be kept more stable.

The invention claimed is:

1. A catalyst system for oxidative dehydrogenation, comprising a fixed-bed reactor filled with a catalyst for oxidative dehydrogenation in an n-stage structure, wherein each stage of the n-stage structure satisfies Equation 1 below:

$$X \text{ wt \%} + Y \text{ wt \%} = 100 \text{ wt \%}, \qquad \text{[Equation 1]}$$

wherein:
- X is an amount of $AB_2O_4$ and is 3 or more and less than 30, wherein A is one or more metals selected from the group consisting of copper (Cu), radium (Ra), barium (Ba), strontium (Sr), calcium (Ca), beryllium (Be), zinc (Zn), magnesium (Mg), manganese (Mn), and cobalt (Co), and B is iron (Fe); and
- Y is an amount of a porous support and is more than 70 and 97 or less;

wherein n is 3 to 8; and wherein the proportion of X is increased by 2 to 3% by weight with each increase in stage number in a direction in which reactants are fed into the reactor.

2. The catalyst system according to claim 1, wherein the $AB_2O_4$ is a coating catalyst coated on the porous support.

3. The catalyst system according to claim 2, wherein the coating catalyst is a binder-free catalyst.

4. The catalyst system according to claim 1, wherein the $AB_2O_4$ is a zinc ferrite, where A is Zn and B is Fe.

5. The catalyst system according to claim 1, wherein the $AB_2O_4$ has an average particle diameter of 0.1 to 250 μm.

6. The catalyst system according to claim 1, wherein the porous support has an average particle diameter of 3 to 9 mm.

7. The catalyst system according to claim 1, wherein the porous support is spherical, hollow, or in a form of pellets.

8. The catalyst system according to claim 1, wherein the porous support is one or more selected from the group consisting of alumina, silica, and zirconia.

9. The catalyst system according to claim 1, wherein the porous support has an average pore size of 50 to 200 μm.

10. The catalyst system according to claim 1, wherein the porous support has a packing density of 0.4 to 3.0 kg/m$^3$.

11. The catalyst system according to claim 1 in which the proportion of X is increased by 2% by weight with each increase in stage number.

12. The catalyst system according to claim 1 in which the proportion of X is increased by 3% by weight with each increase in stage number.

13. A reactor for oxidative dehydrogenation, comprising the catalyst system for oxidative dehydrogenation of claim 1.

14. A method of performing oxidative dehydrogenation, comprising a step of performing oxidative dehydrogenation in the reactor according to claim 13 while continuously passing reactants containing a C4 compound comprising normal butene through a catalyst bed of the reactor.

15. The method according to claim 14, wherein the oxidative dehydrogenation reaction is performed at a reaction temperature of 250 to 500° C. and at a gas hourly space velocity (GHSV) of 50 to 2,000 h$^{-1}$ based on normal butene.

16. The method according to claim 14, wherein the temperature distribution in the catalyst bed due to reaction heat generated during oxidative dehydrogenation exhibits a symmetrical distribution about a center of the catalyst bed.

* * * * *